(12) United States Patent
Yang et al.

(10) Patent No.: US 6,733,520 B2
(45) Date of Patent: May 11, 2004

(54) SANDWICH STRIPED SLEEVE FOR STENT DELIVERY

(75) Inventors: Dachuan Yang, Plymouth, MN (US); Paul J. Miller, St. Paul, MN (US)

(73) Assignee: SciMed Life Systems, Inc., Maple Grove, MN (US)

(*) Notice: Subject to any disclaimer, the term of this patent is extended or adjusted under 35 U.S.C. 154(b) by 0 days.

(21) Appl. No.: 09/829,295

(22) Filed: Apr. 9, 2001

(65) Prior Publication Data

US 2002/0038141 A1 Mar. 28, 2002

Related U.S. Application Data

(63) Continuation-in-part of application No. 09/750,934, filed on Dec. 29, 2000, now abandoned, which is a continuation-in-part of application No. 09/668,496, filed on Sep. 22, 2000, now Pat. No. 6,554,841.

(51) Int. Cl.[7] .................................................. A61F 2/06
(52) U.S. Cl. ....................................... 623/1.12; 606/108
(58) Field of Search ............................... 623/1.11, 1.12, 623/FOR 100; 606/108

(56) References Cited

U.S. PATENT DOCUMENTS

| | | |
|---|---|---|
| 3,825,036 A | 7/1974 | Stent |
| 3,892,314 A | 7/1975 | Semp |
| 4,187,390 A | 2/1980 | Gore |
| 4,773,902 A | 9/1988 | Lentz et al. |
| 4,877,661 A | 10/1989 | House et al. |
| 4,950,227 A | 8/1990 | Savin et al. |
| 5,026,513 A | 6/1991 | House et al. |
| 5,108,416 A | 4/1992 | Ryan et al. |
| 5,156,785 A | 10/1992 | Zdrahala |
| 5,254,089 A | 10/1993 | Wang |
| 5,389,314 A | 2/1995 | Wang |
| 5,403,341 A | 4/1995 | Solar |
| 5,456,674 A | 10/1995 | Bos |
| 5,492,532 A | 2/1996 | Ryan et al. |
| 5,512,051 A | 4/1996 | Wang et al. |
| 5,556,383 A | 9/1996 | Wang et al. |
| 5,634,928 A | 6/1997 | Fischell et al. |
| 5,643,278 A | 7/1997 | Wijay |
| 5,647,848 A | 7/1997 | Jorgensen |
| 5,662,703 A | 9/1997 | Yurek et al. |
| 5,670,558 A | 9/1997 | Onishi et al. |
| 5,690,642 A | 11/1997 | Osborne et al. |
| 5,704,913 A | 1/1998 | Abele et al. |
| 5,749,851 A | 5/1998 | Wang |
| 5,752,934 A | 5/1998 | Campbell et al. |
| 5,788,707 A | 8/1998 | Del Toro et al. |
| 5,792,300 A | 8/1998 | Inderbitzen et al. |
| 5,800,517 A | 9/1998 | Anderson et al. |
| 5,810,871 A | 9/1998 | Tuckey et al. |

(List continued on next page.)

FOREIGN PATENT DOCUMENTS

| | | |
|---|---|---|
| EP | 0 442 657 A2 | 8/1991 |
| EP | 0 688 545 A1 | 12/1995 |
| WO | 97/24403 | 7/1997 |

*Primary Examiner*—David H. Willse
(74) *Attorney, Agent, or Firm*—Vidas Arrett & Steinkraus P.A.

(57) ABSTRACT

The present invention is a stent delivery system including a catheter, wherein the catheter includes an inflatable region. An expandable stent is disposed about at least a portion of the inflatable region. A first end of the at least one stent retaining sleeve covers an end of the stent prior to the stent being expanded for delivery. A second end of the at least one sleeve is engaged to at least a portion of the catheter adjacent to the inflatable region. The at least one stent retaining sleeve is constructed and arranged to longitudinally foreshorten from a first predetermined length to a second predetermined length when the stent is expanded for delivery. The second predetermined length being more than 5 percent shorter than the first predetermined length. When the stent is expanded for delivery, the at least one stent retaining sleeve is retracted off of the stent thereby releasing the stent from the catheter.

30 Claims, 5 Drawing Sheets

U.S. PATENT DOCUMENTS

| | | |
|---|---|---|
| 5,830,182 A | 11/1998 | Wang et al. |
| 5,836,965 A | 11/1998 | Jendersee et al. |
| 5,843,116 A | 12/1998 | Crocker et al. |
| 5,902,631 A | 5/1999 | Wang et al. |
| 5,935,135 A | 8/1999 | Bramfitt et al. |
| 5,944,726 A | 8/1999 | Blaeser et al. |
| 5,951,569 A | 9/1999 | Tuckey et al. |
| 5,968,069 A | 10/1999 | Dusbabek et al. |
| 5,976,120 A | 11/1999 | Chow et al. |
| 5,980,530 A | 11/1999 | Willard et al. |
| 5,980,533 A | 11/1999 | Holman |
| 6,059,813 A | 5/2000 | Vrba et al. |
| 6,063,112 A * | 5/2000 | Sgro ............ 623/1.12 |
| 6,068,634 A | 5/2000 | Cornelius et al. |
| 6,176,875 B1 | 1/2001 | Lenker et al. |
| 6,183,505 B1 | 2/2001 | Mohn, Jr. et al. ......... 623/1.11 |
| 6,221,097 B1 | 4/2001 | Wang et al. |
| 6,387,118 B1 * | 5/2002 | Hanson ............ 623/1.11 |

* cited by examiner

SANDWICH STRIPED SLEEVE FOR STENT DELIVERY

CROSS-REFERENCE TO RELATED APPLICATIONS

This Application is a Continuation in part of application U.S. Ser. No. 09/750,934, filed Dec. 29, 2000, now abandoned, which in-turn is a Continuation in part of U.S. Ser. No. 09/668,496, filed Sep. 22, 2000, issued as U.S. Pat. No. 6,554,841 on Apr. 29, 2003. The entire contents of both applications being incorporated herein by reference.

STATEMENT REGARDING FEDERALLY SPONSORED RESEARCH

Not Applicable

BACKGROUND OF THE INVENTION

1. Field of the Invention

This invention relates to medical device delivery catheters in general, and specifically to balloon catheters for use in delivering a medical device such as a stent to a desired body location, such as in a blood vessel. More specifically, this invention relates to a stent retaining sock or sleeve composed of a matrix of generally elastic material which also includes at least one substantially longitudinally oriented fiber or filament which is harder than the surrounding elastic material and imbedded therein. The filaments may be a singular fiber or be comprised of a braid of several fibers woven together. The combination of the elastomeric sleeve material and reinforcing fiber(s) (braids) provide for a sleeve, which when mounted on a stent delivery balloon catheter, may be expanded in the radial direction during balloon expansion, but which may longitudinally foreshorten during the expansion, thereby causing the ends of the sleeve to retract off of the ends of the stent in a safe and efficient manner.

2. Description of the Related Art

Stents and stent delivery assemblies are utilized in a number of medical procedures and situations, and as such their structure and function are well known. A stent is a generally cylindrical prosthesis introduced via a catheter into a lumen of a body vessel in a configuration having a generally reduced diameter and then expanded to the diameter of the vessel. In its expanded configuration, the stent supports and reinforces the vessel walls while maintaining the vessel in an open, unobstructed condition.

Both self-expanding and inflation expandable stents are well known and widely available in a variety of designs and configurations. Self-expanding stents must be maintained under positive external pressure in order to maintain their reduced diameter configuration during delivery of the stent to its deployment site. Inflation expandable stents may be crimped to their reduced diameter about the delivery catheter, maneuvered to the deployment site, and expanded to the vessel diameter by fluid inflation of a balloon positioned on the delivery catheter. The present invention is particularly concerned with delivery and deployment of inflation expandable stents, although it is generally applicable to self-expanding stents when used with balloon catheters.

In advancing an inflation expandable stent through a body vessel to the deployment site, there are a number of important considerations. The stent must be able to securely maintain its axial position on the delivery catheter, without translocating proximally or distally, and especially without becoming separated from the catheter. The stent, particularly its distal and proximal ends, must be protected to prevent distortion of the stent and to prevent abrasion and/or reduce trauma of the vessel walls.

Inflation expandable stent delivery and deployment assemblies are known which utilize restraining means that overlie the stent during delivery. U.S. Pat. No. 4,950,227 to Savin et al, relates to an expandable stent delivery system in which a sleeve overlaps the distal or proximal margin (or both) of the stent during delivery. That patent discloses a stent delivery system in which a catheter carries, on its distal end portion, a stent which is held in place around the catheter prior to and during percutaneous delivery by means of one and preferably two sleeves. The sleeves are positioned around the catheter with one end portion attached thereto and overlap an end portion(s) of the stent to hold it in place on the catheter in a contracted condition. Each sleeve is elastomeric in nature so as to stretch and release the stent when it expands for implantation. The stent is expandable by means of the expandable balloon on the catheter. During expansion of the stent at the deployment site, the stent margins are freed of the protective sleeve(s). U.S. Pat. No. 5,403,341 to Solar, relates to a stent delivery and deployment assembly which uses retaining sheaths positioned about opposite ends of the compressed stent. The retaining sheaths of Solar are adapted to tear under pressure as the stent is radially expanded, thus releasing the stent from engagement with the sheaths. U.S. Pat. No. 5,108,416 to Ryan et al., describes a stent introducer system which uses one or two flexible end caps and an annular socket surrounding the balloon to position the stent during introduction to the deployment site.

Copending U.S. patent application Ser. No. 09/426,384 which was filed Oct. 26, 1999 and entitled *Longitudinal Dimensional Stable Balloons*, and which is incorporated in its entirety herein by reference describes balloon material having longitudinally oriented fibers.

Copending U.S. patent application Ser. No. 09/407,836 which was filed on Sep. 28, 1999 and entitled *Stent Securement Sleeves and Optional Coatings and Methods of Use*, and which is incorporated in its entirety herein by reference, provides for a stent delivery system having sleeves. In U.S. Ser. No. 09/407,836 the sleeves may be made up of a combination of polytetrafluoroethylene (PTFE) as well as one or more thermoplastic elastomers. Other references exist which disclose a variety of stent retaining sleeves.

In many prior stent delivery systems which utilize retractable sleeves to retain the ends of the stent to the catheter prior to delivery, such as those described above, the expansion characteristics of the sleeves are such that typically the sleeves will foreshorten by less than 5 percent as a result of balloon expansion. This nominal foreshortening may assist in retracting the sleeves off of the stent ends but other attributes such as reduced frictional interface between the sleeve and stent and/or reduced columnar strength of the sleeve may also be required to effectively retract the sleeves from the stent.

As indicated above, a common problem which occurs in catheter assemblies is friction or adhesion between various parts which periodically come into contact with one another during the medical procedure. For instance, friction can occur between the guide catheter and guide wire, between the introducer sheath and the guide catheter, or between the guide catheter and the balloon catheter, for instance, and may increase the difficulty of insertion, cause loss of catheter placement, and result in discomfort to the patient or damage to the vasculature. In catheters equipped with stent retaining socks or sleeves, friction between the balloon and sleeve, and/or the stent and sleeve may also cause retraction of the sleeves to be made more difficult. It is therefore desirable to reduce the friction due to the sliding between the various parts of the catheter assemblies, most notably between the ends of the stent and the portions of the sleeves which retain the ends to the catheter prior to stent implantation.

Copending U.S. application Ser. No. 09/549,286 which was filed Apr. 14, 2000 describes a reduced columnar strength stent retaining sleeve having a plurality of holes. The relatively reduced columnar and radial strength provided by the holes allows the sleeve to be retracted off of a stent without the need for lubricant. However, lubricants may be used to further assist in sleeve retraction.

Lubricants of many types have been used in conjunction with balloon catheters. Both hydrophilic and hydrophobic coatings and lubricants are well known in the catheter art. The present invention may be used in conjunction with any type of lubricious substance suitable for use with a stent delivery catheter, and is further directed to the application of the lubricious substance to the surface of a balloon cone and/or waste subsequent to stent mounting and sleeve placement onto the catheter.

Copending U.S. patent application Ser. No. 09/427,805 filed Oct. 27, 1999, and entitled *End Sleeve Coating for Stent Delivery*, describes the use of stent retaining sleeves having lubricious coatings applied thereto. Copending U.S. patent application Ser. No. 09/273,520 filed Mar. 22, 1999, entitled *Lubricated Sleeve Material For Stent Delivery* likewise describes the use of stent retaining sleeves and lubricants.

The entire content of all patents and applications listed within the present patent application are incorporated herein by reference.

While the various concepts mentioned above as well as those described in the various references cited herein may provide a variety of means for improving sleeve retraction from a stent during balloon expansion, it remains desirable to further improve upon retractable sleeves and stent delivery systems in general. The present invention is directed to a sleeve and/or an associated stent delivery system wherein the sleeve may be readily retracted from a stent as a result of longitudinal foreshortening of the sleeve which occurs during radial expansion.

BRIEF SUMMARY OF THE INVENTION

As indicated above the present invention is directed to a retractable stent retaining sleeve, or pair of sleeves, which may be disposed about the respective ends of a stent to retain the ends of the stent on a stent mounting region of a balloon catheter. The sleeve are retracted off of the stent during the stent delivery process when a balloon or an inflatable portion of the catheter is inflated to radially expand the stent. As the stent is subjected to radial expansion so to is at least a portion of the stent retaining sleeve. The unique construction of the present sleeve provides the sleeves with the capacity to be retracted off of the ends of a stent during balloon expansion to release the stent.

In at least one embodiment of the invention the sleeves are constructed and arranged to foreshorten to an extent greater than previous stent retaining sleeves or socks, thereby providing for improved retraction from the stent ends.

In at least one embodiment of the invention, the length of the sleeves is foreshortened more than 5 percent during sleeve retraction.

In at least one embodiment of the invention, the length of the sleeves is foreshortened 20 percent or more during sleeve retraction.

In at least one embodiment, the instant invention is directed to a medical device delivery system comprising a catheter assembly having a medical device receiving region and at least one retaining sleeve for retaining the medical device on the receiving region prior to delivery. An expandable medical device, such as a stent, is disposed about the medical device receiving region of the catheter assembly. At least one retaining sleeve is disposed about an end of the expandable medical device and at least a portion of the catheter assembly.

In at least one embodiment of the invention, the retractable stent retaining sleeve comprises a first material and a second material, wherein the second material is harder than the first material. The second material may be one or more fibers or braids of fiber of a predetermined material or combination of materials. The fibers may be oriented relative to the longitudinal axis of the retaining sleeve in a variety of patterns. For example the fibers may be substantially parallel to the longitudinal axis of the sleeve, angled relative thereto, helically or otherwise disposed thereabout, etc.

In at least one embodiment of the invention, the fiber(s) or stripe(s) may be disposed about the inside and/or outside of the sleeve.

In yet another embodiment of the invention, the stripes of a second material may be fully enclosed, or "sandwiched" within the matrix of the first material. It should be noted that while the second material may be characterized as being harder than the first material, the second material have additional or alternative features which are different that the first. For example, the first and second material may have different: flexibility, elasticity, tensile modulus, modulus of elasticity, as well as many other characteristics which may be different from one another.

In still another embodiment of the invention the matrix of the sleeve, i.e. the first material, may itself be comprised of a variety of materials, such that the stripe(s) may be enclosed between an inside layer of material and an outside layer of material wherein the inside material and the outside material are different from one another.

BRIEF DESCRIPTION OF THE SEVERAL VIEWS OF THE DRAWINGS

A detailed description of the invention is hereafter described with specific reference being made to the drawings in which.

DETAILED DESCRIPTION OF THE INVENTION

Figure 1:
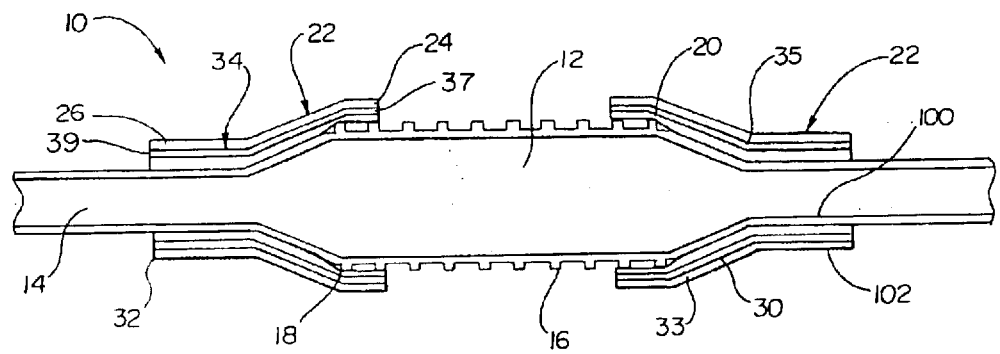
FIG. 1 is a side view of an embodiment of the inventive stent delivery system.

As may be seen in FIG. 1, the present invention may be embodied in a stent delivery catheter, indicated generally at 10. Catheter 10, includes a stent mounting region 12, the stent mounting region 12 may be an inflatable portion of the catheter or may be a separate balloon mounted to the catheter shaft 14. The balloon 12 may be inflatable between an unexpanded state and a fully expanded state. A variety of mechanisms such as inflation lumen(s) (not shown) positioned in or around the shaft 14 and extending from the balloon to the proximal end of the catheter (not shown) may be utilized to fluid inflate the balloon from a remote location outside of a body as is well understood in the art. As is well known, balloons may be initially inflated to a nominal pressure in order to provide the stent delivery system with the familiar shape presently shown. This nominally inflated state is often referred to as the "uninflated" or first inflation state. Similarly, the balloon 12 may be considered to have a fully inflated or second inflation state, such as may be seen in FIGS. 14 and 15, wherein the balloon 12 has been inflated to a predetermined pressure sufficient to expand and delivery the medical device or stent 16 mounted thereon. Depending on the particular characteristics of the balloon 12 as well as the particular characteristics of the device being delivered, the balloon may have a variety of inflation pressures and expansion characteristics.

The stent 16 is disposed about a portion of the balloon 12 prior to delivery when the balloon is inflated to the second or fully inflated state.

The stent 16 includes a proximal end 18 and a distal end 20. In the embodiment shown a first portion 24 of a stent retaining sleeve 22 overlies at least a portion each end 18 and 20. The second portion 26 of the sleeve 22 is engaged to a portion of the catheter shaft 14. As is known in the art, when the balloon 12 and stent 16 are expanded to the delivery state, the first portions 24 of the stent retaining sleeves 22 are configured to retract off of the stent ends 18 and 20.

Figure 14:
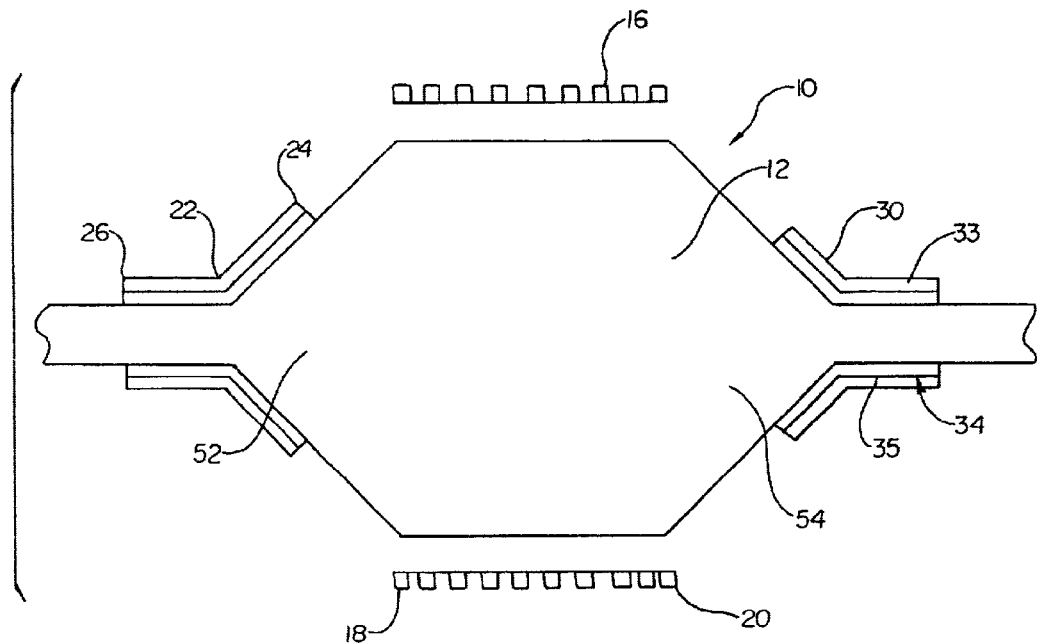
FIG. 14 is a side view of another embodiment of the inventive stent delivery system in the fully inflated or expanded state.
Figure 15:
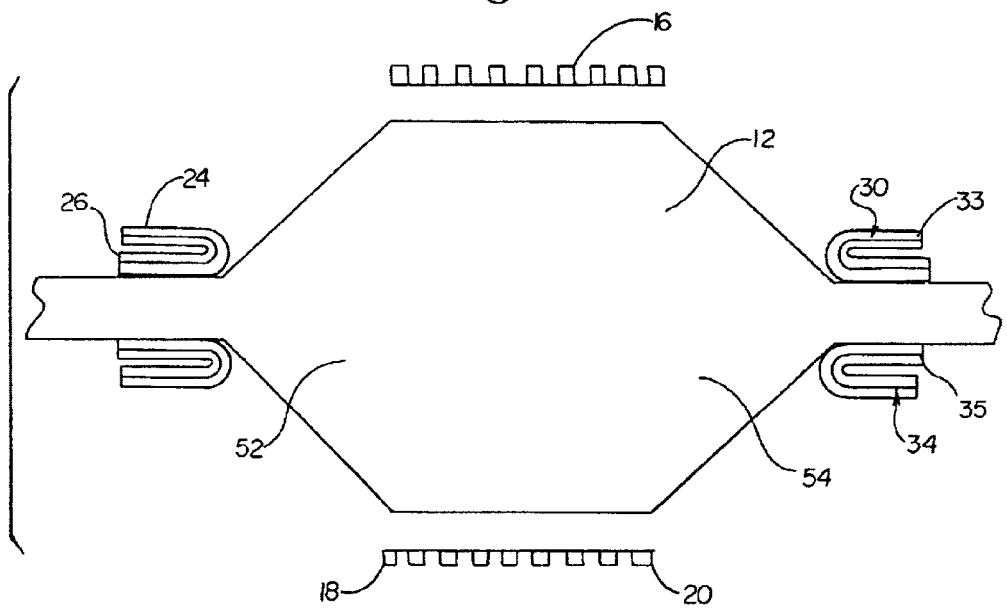
FIG. 15 is a side view of another embodiment of the inventive stent delivery system in the fully inflated or expanded state.

In the present invention however, the sleeves 22 have a unique construction which allows the sleeve 22 to longitudinally foreshorten at least 5 percent or more when the balloon is expanded from the first inflation state shown in FIG. 1 to the fully inflated state such as may be seen in the embodiments shown in FIGS. 14 and 15. The improved foreshortening characteristics of the present sleeves 22 are the result of the unique composite construction of the sleeves 22 which includes a combination of a matrix composed of a matrix material 30, and one or more stripes 35 composed of a stripe material 34.

The matrix material 30 will have a hardness value which on the Shore A durometer scale is less than the hardness value of the stripe material 34. The matrix material 30 is formed into a generally tubular body 32 which provides the sleeve 22 with its shape as well as its inside surface 100 and outside surface 102.

The matrix material 30 may be any elastomer material known which has a hardness as measured by a Shore A durometer of less than 100A (or 55D on the Shore D scale). Preferably, the durometer hardness of the matrix material is between 40A and 100A. The stripe material 34 may be any material having a durometer hardness greater than about 55D. In at least one embodiment of the invention the matrix material 30 has a hardness of 65A and the stripe material 34 has a hardness of 75D.

The harder stripes 35 restrict the elasticity of the matrix 33 such that when the balloon 12 expands to deliver the stent 16 the longitudinal expansion of the sleeve 22 is restricted. Alternatively, the sleeve 22 may be provided with a negative expansion. Such that when the balloon is expanded to deliver the stent 16, rather than longitudinally stretch or expand, the sleeves 22 will foreshorten from a first sleeve length at the first inflation state to a second shorter length in the second inflation state. The sleeves 22 may be constructed to foreshorten at least 5 percent to 20 percent or more.

Figure 2:
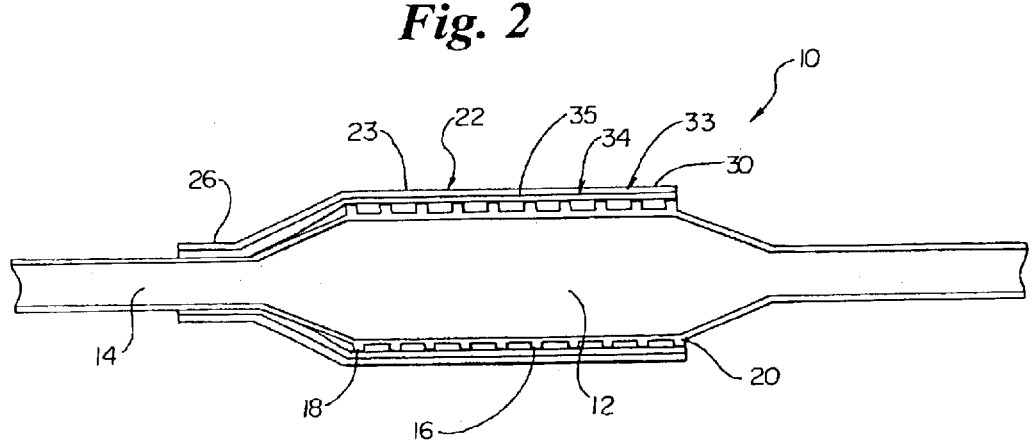
FIG. 2 is a side view of another embodiment of the inventive stent delivery system.

The ability to foreshorten to the extent described above provides the sleeve 22 with improved retraction characteristics. As a result, rather than providing a stent 16 with sleeves at both ends 18 and 20, a single longer sleeve 22 such as is shown in the embodiment of FIG. 2 may have a first portion 23 which overlies both ends 18 and 20 of the stent. When the balloon 12 is inflated to expand and deliver the stent 16 the entire sleeve 22 is withdrawn off of the stent 16. In the embodiment shown, the second portion 26 of the sleeve 22 is engaged to a portion of the shaft 14 proximal to the balloon 12. As a result, when the balloon 12 is inflated to deliver the stent 16, the sleeve 22 will foreshorten and retract off of the stent in the proximal direction. It should be noted however, that in an alternative embodiment the single sleeve 22 may be positioned distal of the stent 16 for distal retraction therefrom.

As may be seen in FIGS. 1 and 2, the stripe component 35 is imbedded in the matrix 33 and the longitudinal length of the stripe 35 is completely surrounded therein. However, the ends 37 and 39 of the stripe 35 may be exposed at the ends of the sleeve 24 and 26 respectively. Alternatively the matrix material 34 may overlap the ends 37 and 39 of the stripe 35 thereby completely enveloping the entire surface of the stripe 35.

The number of stripes 35 may vary from a single stripe 35 such as may be seen in FIGS. 1 and 2 to several stripes as shown in the various embodiments of the unexpanded or preinflation state sleeves 22 depicted in FIGS. 3–10. In FIGS. 3–8 it may be seen that the stripes 35 may have a wide variety of orientations and positions relative to the matrix 33. The embodiments depicted in FIGS. 3–10 are just several examples of the configurations which may be utilized. One of skill in the art will recognize that the present invention is also directed to all other configurations, orientations and numbers of strips 35 which may be utilized with the matrix 33.

Figure 3:
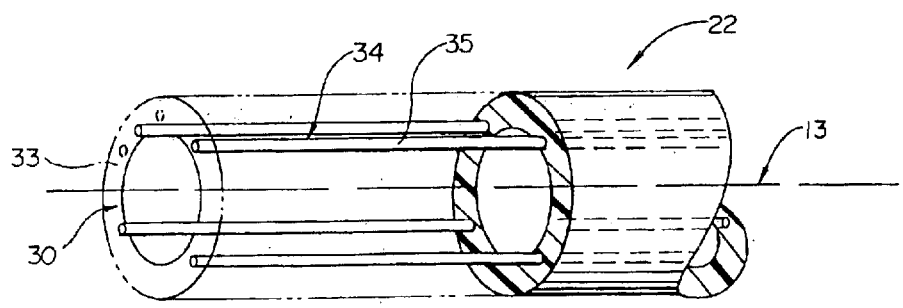
FIG. 3 is a partial cut-away perspective view of an embodiment of the retractable sleeve of the present invention.

In FIG. 3, the stripes 35 are imbedded within the matrix 33 and extend the entire length of the sleeve 22. In the present embodiment, prior to being mounted on the stent delivery catheter the stripes 35 are oriented within the matrix 33 to be parallel to the longitudinal axis 13 of the sleeve 22.

Figure 4:
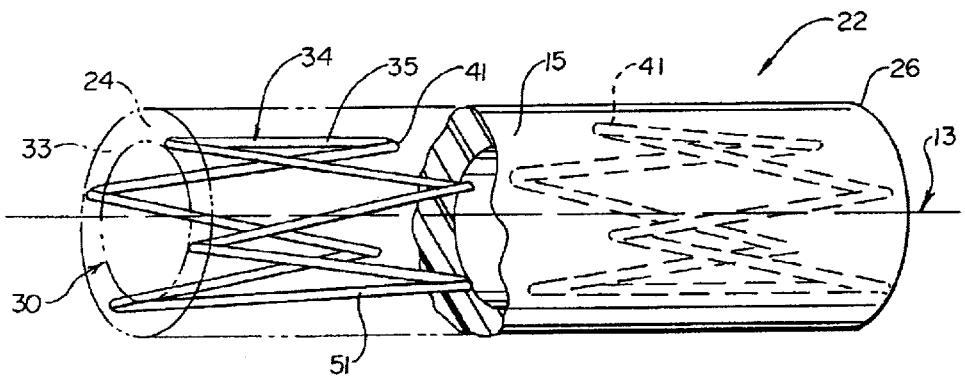
FIG. 4 is a partial cut-away perspective view of another embodiment of the retractable sleeve of the present invention.

In the embodiment shown in FIG. 4, a pair of stripes 35 are configured within the matrix 33 in opposing zig-zag patterns. The stripes 35 extend from a respective end 24 or 26 of the sleeve 22 and extend to a middle portion 15 of the sleeve 22 and then extend back toward the respective sleeve end in an alternating pattern. In the embodiment shown, the zig-zag configured stripes 35 may be made up of individual lengths 51 whose ends are adjacent to one another near the respective ends 24 and 26, or middle portion 15 of the sleeve 22. Alternatively, a single zig-zag stripe 35 may be employed which is a continuous strand having a plurality of folds 41 at the sleeve ends 24 and 26 to provide the pattern shown.

Figure 5:
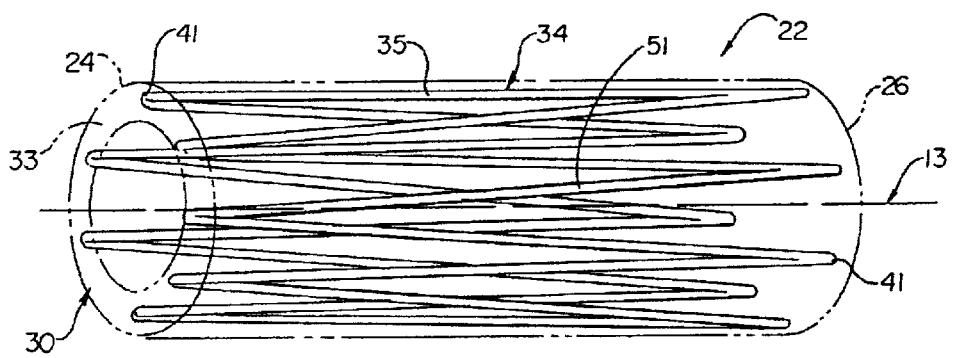
FIG. 5 is a partial cut-away perspective view of another embodiment of the retractable sleeve of the present invention.

Similar to the embodiment shown in FIG. 4, in the embodiment shown in FIG. 5, the stripes 35 are in a zig-zag pattern wherein the stripe 35 (or lengths 51 thereof) which are angularly disposed relative to the longitudinal axis 13 of the sleeve 22. However, in FIG. 5 the stripes 35 (or lengths 51 thereof) fully extend from one end 24 of the sleeve 22 to the other 26.

The unique in a multiple zig-zag pattern of the stripes 35 such as may be seen in FIG. 5 may assist the sleeves in attaining an S-fold configuration when retracted off of the stent ends 18 and 22 such as may be seen in FIG. 14.

Figure 6:
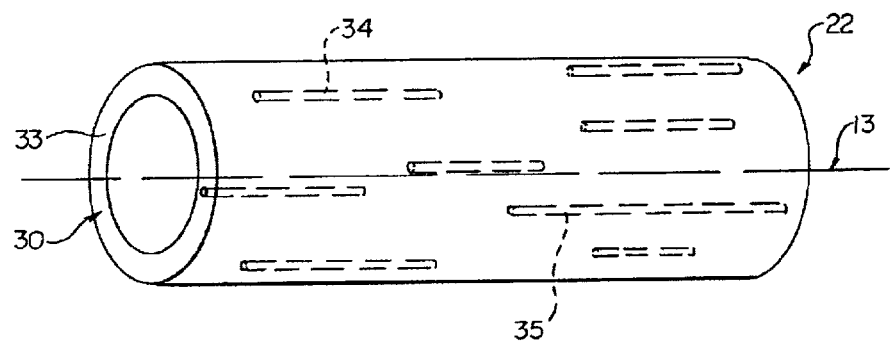
FIG. 6 is a partial cut-away perspective view of another embodiment of the retractable sleeve of the present invention.

In FIG. 6, an embodiment of the sleeve is shown wherein each of the plurality of stripes 35 have a random length which may or may not extend the entire length of the sleeve 22. Additionally, the individual stripes 35 may or may not be parallel to the longitudinal axis 13, and may have a completely random orientation relative to the longitudinal axis 13. It should also be noted that the stripes 35 may or may not be arranged in a uniform pattern such as is shown in the previously described embodiments.

Figure 7:
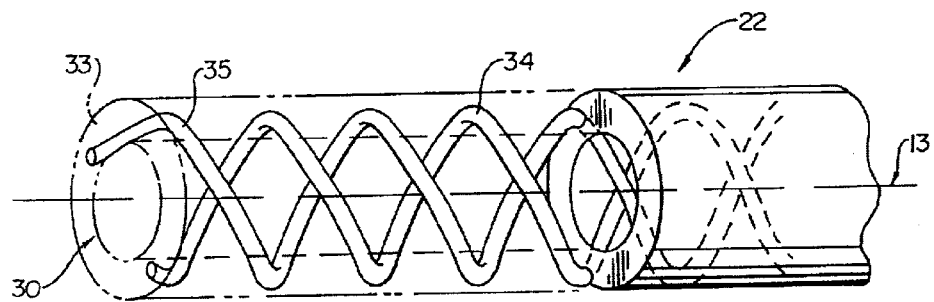
FIG. 7 is a partial cut-away perspective view of another embodiment of the retractable sleeve of the present invention.
Figure 8:
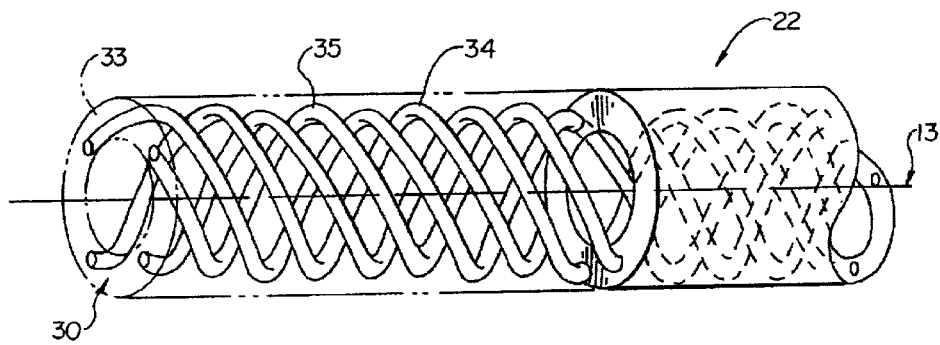
FIG. 8 is a partial cut-away perspective view of another embodiment of the retractable sleeve of the present invention.

In FIG. 7, a pair of strands 35 are shown in a double helix configuration wherein each strand 35 is helically disposed relative to the longitudinal axis 13 in opposing directions. In the embodiment shown in FIG. 8 a plurality of helically disposed strands 35 are imbedded in the matrix 33, wherein each of the strands 35 is oriented in the same direction.

Where the strands or stripes 35 are arranged in a helical pattern in between the matrix 33, the strands 35 will provide a significant foreshortening effect as the strands arranged widely in the longitudinal direction. Preferably, the strands 35 should not be arranged such that they affect the radial expansion of the matrix 33. While a wide variety of strand 35 configurations may be used, at least one configuration such as a double helix of a relatively wide open arrangement where strands 35 are no more than 30 degrees angularly disposed relative to the longitudinal axis 13 of the sleeve 22, may provide improved foreshortening characteristics.

Figure 9:
FIG. 9 is a perspective view of another embodiment of the retractable sleeve of the present invention.
Figure 10:
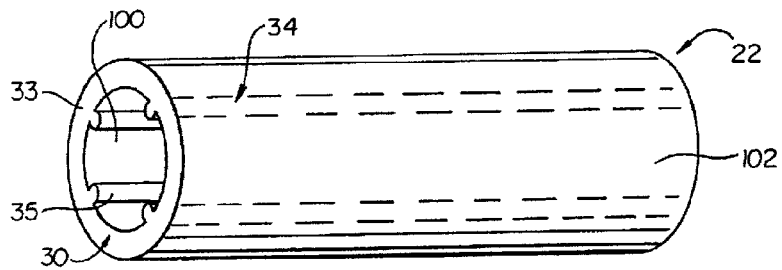
FIG. 10 is a perspective view of another embodiment of the retractable sleeve of the present invention.

In FIGS. 9–10 embodiments of the sleeve 22 are shown wherein the stripes 35 need not be completely imbedded within the matrix 33. In FIG. 9, the stripes 35 are engaged to the inner surface 100 of the matrix 33, whereas in FIG. 10 the stripes 35 are engaged to the outer surface 102 of the matrix 33. Whether engaged to the inside 100 or outside surface 102, the matrix 33 may partially surround the stripes 35. Alternatively or in addition, the stripes 35 may be secured to the respective surface 100 and 102 in a variety of manners. For example, chemical adhesives, heat welding by laser or other means, chemical welding, etc, or other securing methods may all be used to secure the stripes 35 to the respective surfaces 100 and 102 of the matrix 33. However, in a preferred embodiment, the matrix material 30 and the stripe material 34 are coextruded. It should also be noted that in an alternative embodiment one or more stripes may be engaged to the inner surface of the matrix, the outer surface of the matrix, and/or imbedded within the matrix or any combination thereof. Regardless of the position of the stripes within the matrix or on of its surfaces, the stripes may be positioned in any of the variety of configurations and orientations described herein.

In any of the embodiments described and/or depicted herein, the matrix material 30 may be selected from a wide variety of substances. For example the matrix may include, but is not limited to, one or more of the following substances: soft grade polyester/polyether elastomers such as Arnitel™ available from DSM Engineering, polyurethane-polyether polymers, such as Tecothane™ 1074A available from Thermedics, Inc.; polyester-polyurethanes, such as Pellethane™ 2102-75A sold by Dow Chemical; polyester-polyurethanes, such as Estane™ 5703P sold by BF Goodrich; polyether block amides, such as Pebax™ 2533 and 3533 available from Elf Atochem; and styrene-butadienstyrene triblock copolymers such as Kraton™ D1101 sold by Shell Chemical company. Other materials which may also be used in the production of the matrix material 30 include, but are not limited to styrenic block copolymers, polyurethanes, silicone rubber, natural rubber, copolyesters, polyamides, EPDM rubber/polyolefin, nitril rubber/PVC, fluoroelastomers, butyl rubber, epichlorohydrin, soft block copolymers, and any combinations thereof.

The stripe material 34 may also be selected from a wide range of materials. For example the stripe material 34 may be include, but is not limited to, one or more of the following substances: polyethyleneterephthalate (PET), polybutylene terephthalate (PBT), polytrimethylene terephthalate (PTT), Nylon™, engineering thermoplastic polyurethanes, fluoropolymers, polyester/polyether elastomers such as Arnitel™ available from DSM Engineering, polyurethane-polyether polymers, such as Tecothane™ 1055D or 1075D, Tecoplast™ 470 both of which are available from Thermedics, Inc.; polyesterpolyurethanes, such as Estane™ 58170 sold by BF Goodrich; polyether block amides, such as Pebax™ 7233 or 6333 both of which are available from Elf Atochem. Other materials which may also be used in the production of the stripe material 34 include, but are not limited to: polyolefins, polystyrene, polyvinyl chloride, acrylonitrile-butadiene-styrene polymers, polyacrylonitrile, polyacrylate, vinyl acetate polymer, cellulose plastics, polyurethanes, polyethylene terephthalate, polyacetal, polyethers, polycarbonates, polyamides, polyphenylene sulfide, polyarylethersulfones, polyaryletherketones, polytetrafluoroethylene, and any combinations thereof.

The above examples of the matrix and stripe materials 30 and 34 respectively, are in no way exhaustive of the potential substances or combinations of substances which may be used. The present invention is directed to a sleeve 22 composed of any materials which have the qualities previously described for the respective materials 30 and 34.

Figure 11:
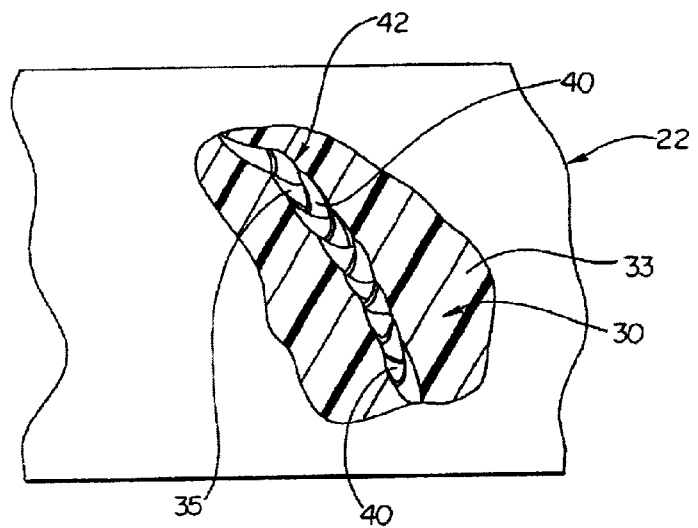
FIG. 11 is a detailed partially cut-away view of another embodiment of the retractable sleeve of the present invention.

As may be seen in the various figures, the present invention may be embodied in a variety of manners. Similarly the sleeves 22 themselves may be provided in a wide range of striped configurations. As may be seen in FIG. 11, the stripes 35 themselves may also be provided in a variety of designs. In FIG. 11, a close-up view of a stripe 35 is shown within the surrounding matrix 33. The stripe 35 is made up of a plurality of interwoven fibers 40 which are woven together to form a braid structure 42. The braided configuration of the stripe 35 provides the sleeve 22 with a stripe or stripes 35 that may be substantially stronger than a single monofilament fiber 40, while maintaining the desired hardness and flexibility characteristics of the stripe material 34. As a result the sleeve 22 with one or more braids 42 of a given stripe material 34 shown will have improved longitudinal strength characteristics without a reduction in flexibility which may have resulted if a harder material 34 were used to form the stripe 35. In addition, where the stripe 35 is a braid 42 of several fibers 40, the individual fibers may be materials different from one another.

Figure 12:
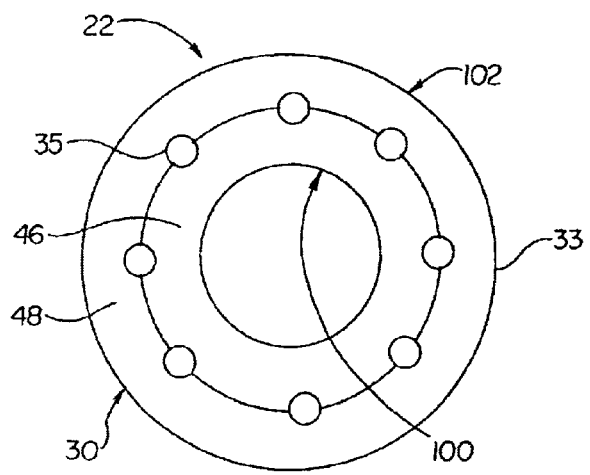
FIG. 12 is a cross-sectional view of another embodiment of the retractable sleeve of the present invention.

Not only are the stripes 35 variable in their characteristics, but the matrix 33 may also be provided in alternative forms. In FIG. 12, an embodiment of the sleeve 22 is shown wherein the matrix material 30 is actually a combination of materials. In the embodiment shown, the matrix 33 is a combination of an inner material 46 and an outer material 48, with a plurality of stripes 35 sandwiched in between. Providing the matrix 33 with a combination of materials may provide the sleeve 22 with even greater improvements for retraction of the sleeve. For example, the inner material 46 may be a layer of hydrophobic elastomer, such as a Siloxane-Polyurethane copolymer, which has a relatively low surface friction and less tack, thereby providing the sleeve 22 with a reduced frictional interface between the inner surface 100 of the sleeve 22 and the stent 16 and/or balloon 12 (shown in FIG. 1). The outer material 48 may be comprised of a hydrophilic elastomer, such as hydrophilic polyurethane, which may provide the outer surface 102 of the sleeve 22 with wet lubricity characteristics when the outer surface is in contact with bodily fluids, such as when the catheter is advanced through a vessel. In addition to the example provided, it should be noted that the inner material 46 and the outer material 48 of the sleeve 22 may be provided with a wide variety of different or similar material combinations.

Figure 13:
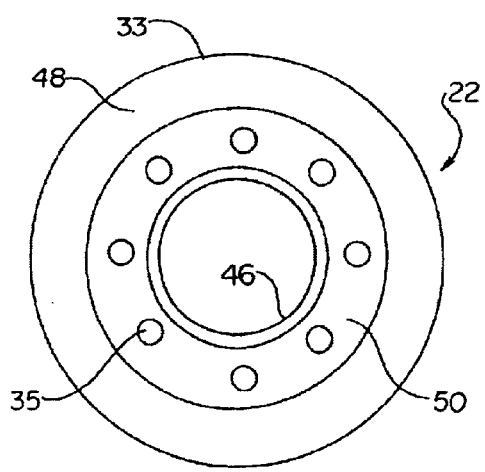
FIG. 13 is a cross-sectional view of another embodiment of the retractable sleeve of the present invention.

In FIG. 13 another embodiment is shown wherein the matrix 33 is comprised of three layers, with the stripes completely imbedded within an intermediate layer 50, which is in turn sandwiched between the outer material 48 and inner material 46. Such an embodiment may be useful when the materials selected for the outer material 48 and inner material 46 do not tend to readily bond together and an intermediate material 50 is used to provide a material which the outer material 48 and inner material 46 may be more readily bonded to. The matrix 33 is not limited to only the one, two or three layer configurations described herein, but may be embodied in a wide range of configurations having a plurality of layers of one or more materials.

The sleeves 22 may be provided in a wide range of shapes and sizes. The sleeves may have surface features such as dimples or troughs, or may have structural alterations such as through holes or ports, for altering the retraction characteristics of the sleeve. The sleeve 22 may include additional layers such as internal or external coatings, such as may be known in the art for improving the sleeve's as well as the catheter's performance. In addition to the above, the sleeves may be provided with any of the variety of retraction configurations which may be known. For example, in FIG. 14 the sleeves 22 are designed to retract off of the stent ends 18 and 20 when the balloon 12 is inflated to deliver the stent 16, but the first portion 24 of each of the sleeves 22 continues to overlay the cone portions 52 and 54, respectively, of the balloon 12. Such a configuration may be useful in collapse and rewrap of the balloon subsequent to stent delivery.

In an alternative embodiment shown in FIG. 15, sleeves 22 are configured to retract completely off of the stent 16 as well as the balloon cones 52 and 54.

In alternative embodiments, notably those utilized specifically for delivery of a self expanding stent, a retractable sheath (not shown) such as are known in the art, may be employed to overlay the stent. In such embodiments a single sleeve or two sleeves such have been shown and described may be employed to retain the self-expanding stent in place. When the sheath is retracted the stent will expand causing the sleeve(s) to retract.

In addition to being directed to the embodiments described above and claimed below, the present invention is further directed to embodiments having different combinations of the features described above and claimed below. As such, the invention is also directed to other embodiments having any other possible combination of the dependent features claimed below.

The above examples and disclosure are intended to be illustrative and not exhaustive. These examples and description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

What is claimed is:

1. A stent delivery system comprising:
   a catheter including a stent mounting region, the stent mounting region being inflatable from a first inflation state to a second inflation state;
   a stent disposed about the stent mounting region of the catheter, the stent having a distal end and a proximal end, the stent further having a first expanded state and a second expanded state, and
   at least one stent retaining sleeve, the at least one stent retaining sleeve having a first end and a second end, the first end overlying an end of the stent prior to the stent being placed in the second expanded state, the second end engaged to at least a portion of the catheter adjacent to the stent mounting region, the at least one stent retaining sleeve constructed and arranged to longitudinally foreshorten from a first predetermined length in the first inflation state to a second predetermined length in the second inflation state, the second predetermined length being more than 5 percent shorter than the first predetermined length, further wherein in the second inflation state the stent is in the second expanded state and the first end of the at least one stent retaining sleeve is retracted off of the stent thereby releasing the stent from the catheter, wherein the at least one sleeve is constructed from a combination of a matrix of a matrix material formed into a tube and a plurality of elongate stripes, the elongate stripes being made of a stripe material, each elongate stripe being engaged to the matrix, wherein no elongate stripe is interwoven with any other elongate stripe.

2. The stent delivery system of claim 1 wherein the second predetermined length is at least 10 percent shorter than the first predetermined length.

3. The stent delivery system of claim 1 wherein the second predetermined length is at least 20 percent shorter than the first predetermined length.

4. The stent delivery system of claim 1 wherein the matrix material and the stripe material have different material characteristics.

5. The stent delivery system of claim 1 wherein the at least one elongate stripe is substantially parallel to a longitudinal axis of the at least one sleeve in an unexpanded state.

6. The stent delivery system of claim 5 wherein the at least one elongate stripe has a length substantially equal to that of the matrix.

7. The stent delivery system of claim 1 wherein the at least one elongate stripe is characterized as being oriented in a helical manner relative to the matrix.

8. The stent delivery system of claim 1 wherein the at least one stripe extends back and forth in a repeating manner from the first end of the at least one sleeve to the second end of the at least one sleeve at a predetermined angle relative to a longitudinal axis of the at least one sleeve.

9. The stent delivery system of claim 1 wherein the at least one stripe comprises a first stripe and a second stripe, the first stripe extending back and forth in a repeating manner from the first end of the at least one sleeve to a middle portion of the at least one sleeve at a predetermined angle relative to a longitudinal axis of the at least one sleeve, the second stripe extending back and forth in a repeating manner from the second end of the at least one sleeve to the middle portion of the at least one sleeve at a second predetermined angle relative to the longitudinal axis of the at least one sleeve.

10. The stent delivery system of claim 9 wherein the first predetermined angle and the second predetermined angle are the same.

11. The stent delivery system of claim 1 wherein each elongate stripe is constructed of a plurality of fibers of the stripe material woven together to form a braid.

12. The stent delivery system of claim 11 wherein at least one of the plurality of elongate stripes is substantially parallel to a longitudinal axis of the at least one sleeve in an unexpanded state.

13. The stent delivery system of claim 11 wherein at least one of the plurality of elongate stripes is oriented in a helical manner to the matrix.

14. The stent delivery system of claim 11 wherein the plurality of elongate stripes extend back and forth from the first end of the at least one sleeve to the second end of the at least one sleeve, each of the plurality of elongate stripes being disposed at a predetermined angle relative to a longitudinal axis of the at least one sleeve.

15. The stent delivery system of claim 11 wherein each of the plurality of elongate stripes has a predetermined length different from one another.

16. The stent delivery system of claim 11 wherein the plurality of elongate stripes are distributed throughout the matrix in a uniform manner.

17. The stent delivery system of claim 11 wherein each of the plurality of elongate stripes have a uniform orientation relative to a longitudinal axis of the at least one sleeve.

18. The stent delivery system of claim 11 wherein the plurality of elongate stripes are distributed throughout the matrix randomly.

19. The stent delivery system of claim 11 wherein each of the plurality of elongate stripes have a uniform orientation relative to a longitudinal axis of the at least one sleeve.

20. The stent delivery system of claim 11 wherein the plurality of elongate stripes are distributed randomly throughout the matrix.

21. The stent delivery system of claim 11 wherein each of the plurality of elongate stripes have a randomly determined orientation relative to a longitudinal axis of the at least one sleeve.

22. The stent delivery system of claim 1 wherein the at least one elongate stripe is substantially enclosed by the matrix.

23. The stent delivery system of claim 1 wherein the matrix has an outside surface, the at least one elongate stripe being engaged to the outside surface of the matrix.

24. The stent delivery system of claim 1 wherein the matrix has an inside surface, the at least one elongate stripe being engaged to the inside surface of the matrix.

25. The stent delivery system of claim 1 wherein the matrix material further comprises a plurality of matrix layers, each of the plurality of matrix layers being a different material.

26. The stent delivery system of claim 25 wherein the plurality of matrix layers comprise an inner matrix layer and an outer matrix layer.

27. The stent delivery system of claim 26 wherein the at least one elongate stripe is positioned between at least a portion of the inner matrix layer and the outer matrix layer.

28. The stent delivery system of claim 26 wherein the plurality of matrix layers further comprise an intermediate matrix layer positioned between the inner matrix layer and the outer matrix layer, the at least one elongate stripe being substantially enclosed within the intermediate matrix material.

29. The stent delivery system of claim 1 wherein the matrix material is selected from at least one member of the group consisting of: styrenic block copolymers, polyurethanes, silicone rubber, natural rubber, copolyesters, polyamides, EPDM rubber/polyolefin, nitril rubber/PVC, fluoroelastomers, butyl rubber, epichlorohydrin, and any combinations thereof.

30. The stent delivery system of claim 1 wherein the stripe material is selected from at least one member of the group consisting of: liquid crystal polymers, polyolefins, polystyrene, polyvinyl chloride, acrylonitrile-butadiene-styrene polymers, polyacrylonitrile, polyacrylate, vinyl acetate polymer, cellulose plastics, polyurethanes, polyethylene terephthalate, polyacetal, polyethers, polycarbonates, polyamides, polyphenylene sulfide, polyarylethersulfones, polyaryletherketones, polytetrafluoroethylene, polyethyleneterephthalate, nylon, metal, carbon, glass and any combinations thereof.

* * * * *